(12) United States Patent
Shinohara et al.

(10) Patent No.: US 10,822,826 B2
(45) Date of Patent: Nov. 3, 2020

(54) FACTORY FOR MANUFACTURING ABSORBENT ARTICLE

(71) Applicant: Unicharm Corporation, Ehime (JP)

(72) Inventors: Tetsushi Shinohara, Kanonji (JP); Yoshihiko Matsumoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 16/465,821

(22) PCT Filed: Dec. 16, 2016

(86) PCT No.: PCT/JP2016/087640
§ 371 (c)(1),
(2) Date: May 31, 2019

(87) PCT Pub. No.: WO2018/109941
PCT Pub. Date: Jun. 21, 2018

(65) Prior Publication Data
US 2019/0301190 A1    Oct. 3, 2019

(51) Int. Cl.
*B65H 19/12* (2006.01)
*E04H 5/02* (2006.01)
*A61F 13/15* (2006.01)

(52) U.S. Cl.
CPC .............. *E04H 5/02* (2013.01); *A61F 13/15* (2013.01); *A61F 13/15764* (2013.01); *B65H 19/12* (2013.01)

(58) Field of Classification Search
CPC .................................. E04H 5/02; B65H 9/12
(Continued)

(56) References Cited

U.S. PATENT DOCUMENTS 3,984,272 A * 10/1976 Teed ...................... A41B 13/00
156/201
4,048,769 A * 9/1977 van der Lely ...... E04B 1/34823
52/79.7
(Continued)

FOREIGN PATENT DOCUMENTS

EP         2491909 A1      8/2012
JP      2000201958 A       7/2000

OTHER PUBLICATIONS

Written Opinion of the International Searching Authority issued in corresponding application No. PCT/JP2016/087460 dated Feb. 21, 2017 (4 pages).
(Continued)

*Primary Examiner* — Paola Agudelo
(74) *Attorney, Agent, or Firm* — Osha Liang LLP

(57) ABSTRACT

A factory for manufacturing an absorbent article includes a building that includes an upper story and a lower story located below the upper story. The upper story and lower story include a floor, a wall provided along an entire periphery of the floor, an illumination device provided on a ceiling, and an air conditioner having an air outlet for discharging air, respectively. An opening is formed in the floor of the upper story. The upper story includes a paying-out device to which a material coil on which a nonwoven fabric is wound is attached and that pays out the nonwoven fabric. The nonwoven fabric serves as at least one type among a plurality of types of materials. The lower story includes a processing section that processes the plurality of types including the nonwoven fabric that is transported from the upper story through the opening.

10 Claims, 11 Drawing Sheets

VIEW IN DIRECTION OF ARROWS III-III

(58) Field of Classification Search
USPC .................................................... 52/236.3
See application file for complete search history.

(56) References Cited

U.S. PATENT DOCUMENTS

| | | | | |
|---|---|---|---|---|
| 4,136,492 A | * | 1/1979 | Willingham | ........ E04B 1/34823 |
| | | | | 52/30 |
| 4,331,501 A | * | 5/1982 | Teed | ................. A61F 13/15593 |
| | | | | 156/176 |
| 4,783,231 A | * | 11/1988 | Raley | ....................... D04H 3/16 |
| | | | | 156/167 |
| 6,390,167 B1 | * | 5/2002 | Geissen | ............ A61F 13/15764 |
| | | | | 156/219 |
| 2005/0257881 A1 | * | 11/2005 | Coose | ............... A61F 13/15804 |
| | | | | 156/256 |
| 2011/0146164 A1 | * | 6/2011 | Haney | ....................... E04H 1/00 |
| | | | | 52/79.1 |
| 2013/0056576 A1 | * | 3/2013 | Andrews | ........... A61F 13/15723 |
| | | | | 242/560 |
| 2014/0137486 A1 | * | 5/2014 | Driess | .................... E04H 1/005 |
| | | | | 52/30 |

OTHER PUBLICATIONS

International Preliminary Report on Patentability issued in corresponding International application No. PCT/JP2016/087640 dated Jun. 18, 2019 (7 pages).
Extended European Search Report issued in corresponding European Application No. 16923698.1, dated Nov. 22, 2019 (5 pages).
Office Action issued in the corresponding European Patent Application No. 16923698.1, dated Aug. 5, 2020 (4 pages).

* cited by examiner

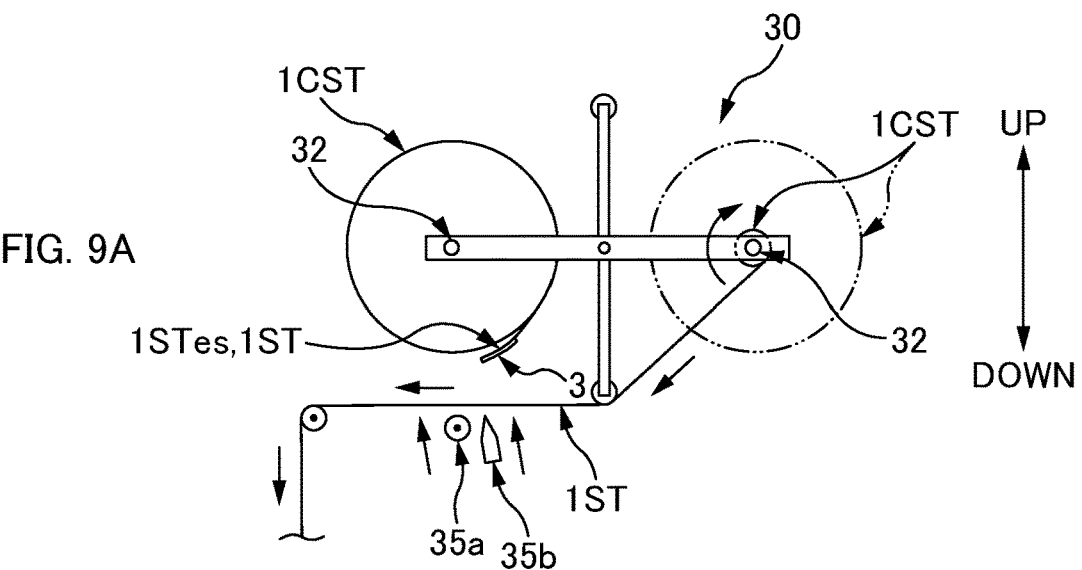
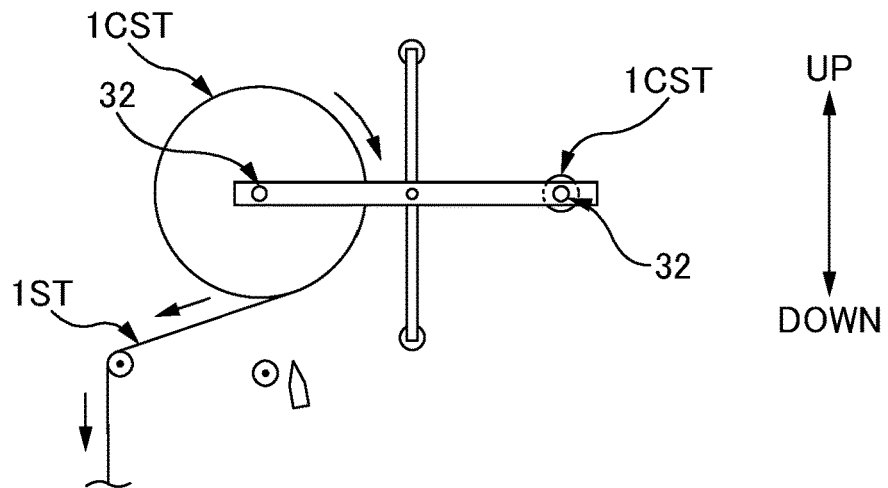
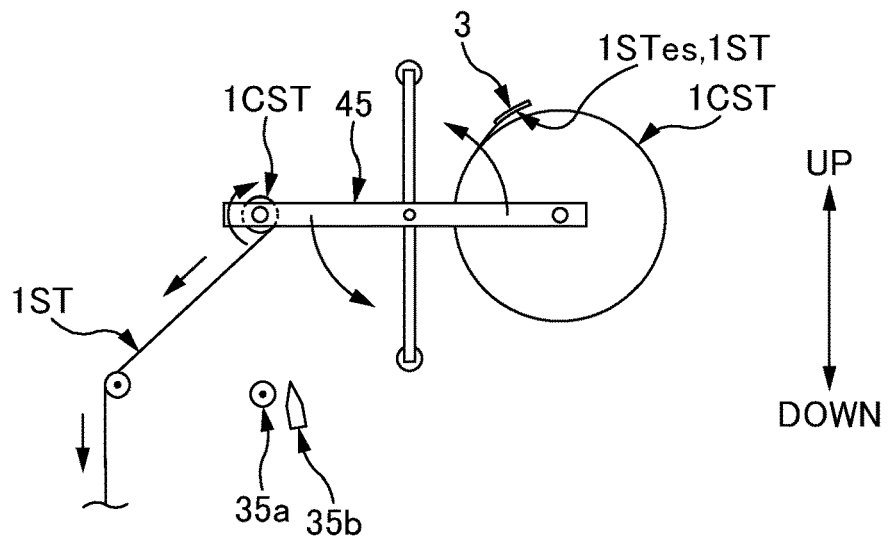

FACTORY FOR MANUFACTURING ABSORBENT ARTICLE

TECHNICAL FIELD

The present invention relates to a factory for manufacturing an absorbent article such as a disposable diaper or a sanitary napkin.

BACKGROUND ART

In existing factories for manufacturing an absorbent article such as a disposable diaper or a sanitary napkin, the article is manufactured by using a plurality of types of materials.

PTL 1 discloses, as an example of a building of the factory, a so-called mezzanine-style building, that is, a two-story building with an intermediate story. On the intermediate story, paying-out devices that respectively pay out the materials from a plurality of types of material coils are disposed to correspond to the types, and the materials that are paid out are transported and supplied to the first story. Processing sections are provided on the first story. The processing sections perform various processing operations, such as pressing and joining, on the plurality of types of materials supplied from the intermediate story while transporting the materials, thereby manufacturing an absorbent article.

CITATION LIST

Patent Literature

[PTL 1] European Patent Application Publication No. 2491909

SUMMARY OF INVENTION

Technical Problem

In particular, when the material is a nonwoven fabric, lint is scattered when paying out the material from the material coil. However, since the building described in PTL 1 is a mezzanine-style building, the intermediate story and the first story are not sufficiently separated from each other by a wall.

Therefore, lint that is scattered on an upper story, which is the intermediate story, tends to enter a lower story, which is the first story. As a result, the lint tends to contaminate the lower story, where the processing sections are located, that is, the lower story tends to enter a state in which lint is suspended in the air. Then, the lint tends to adhere to another material transported on the lower story and contaminate this material. As a result, it is likely that an absorbent article that is manufactured becomes defective due to adhesion of the lint to the material.

The present invention has been made in consideration of the problem described above, and an object thereof is to suppress the occurrence of a problem of lint, which may be scattered when a nonwoven fabric as a type of material is paid out from a material coil, adhering to another material on a lower story that has a processing section and contaminating the other material.

Solution to Problem

A main aspect of the present invention for achieving the above-described aspect is a factory for manufacturing an absorbent article by using a plurality of types of materials, including:

a building including: an upper story; and a lower story located below the upper story, the upper story including: a floor; a wall provided along an entire periphery of the floor; an illumination device provided on a ceiling; and an air conditioner having an air outlet for discharging air, the lower story including: a floor; a wall provided along an entire periphery of the floor; an illumination device provided on a ceiling; and an air conditioner having an air outlet for discharging air, an opening through which the upper story and the lower story communicate being formed in the floor of the upper story, the upper story further including a paying-out device to which a material coil on which a nonwoven fabric is wound is attached and that pays out the nonwoven fabric, the nonwoven fabric serving as at least one type among the plurality of types of materials, the lower story further including a processing section that processes the plurality of types of materials including the nonwoven fabric that is transported from the upper story through the opening.

Features of the present invention other than the above will become clear by reading the description of the present specification with reference to the accompanying drawings.

Advantageous Effects of Invention

According to the present invention, it is possible to suppress the occurrence of a problem of lint, which may be scattered when a nonwoven fabric as a type of material is paid out from a material coil, adhering to another material on a lower story that has a processing section and contaminating the other material.

Solution to Problem

BRIEF DESCRIPTION OF THE DRAWINGS

FIGS. 9A to 9C illustrate a type-2 paying-out device 30.

DESCRIPTION OF EMBODIMENTS

Figure 1:
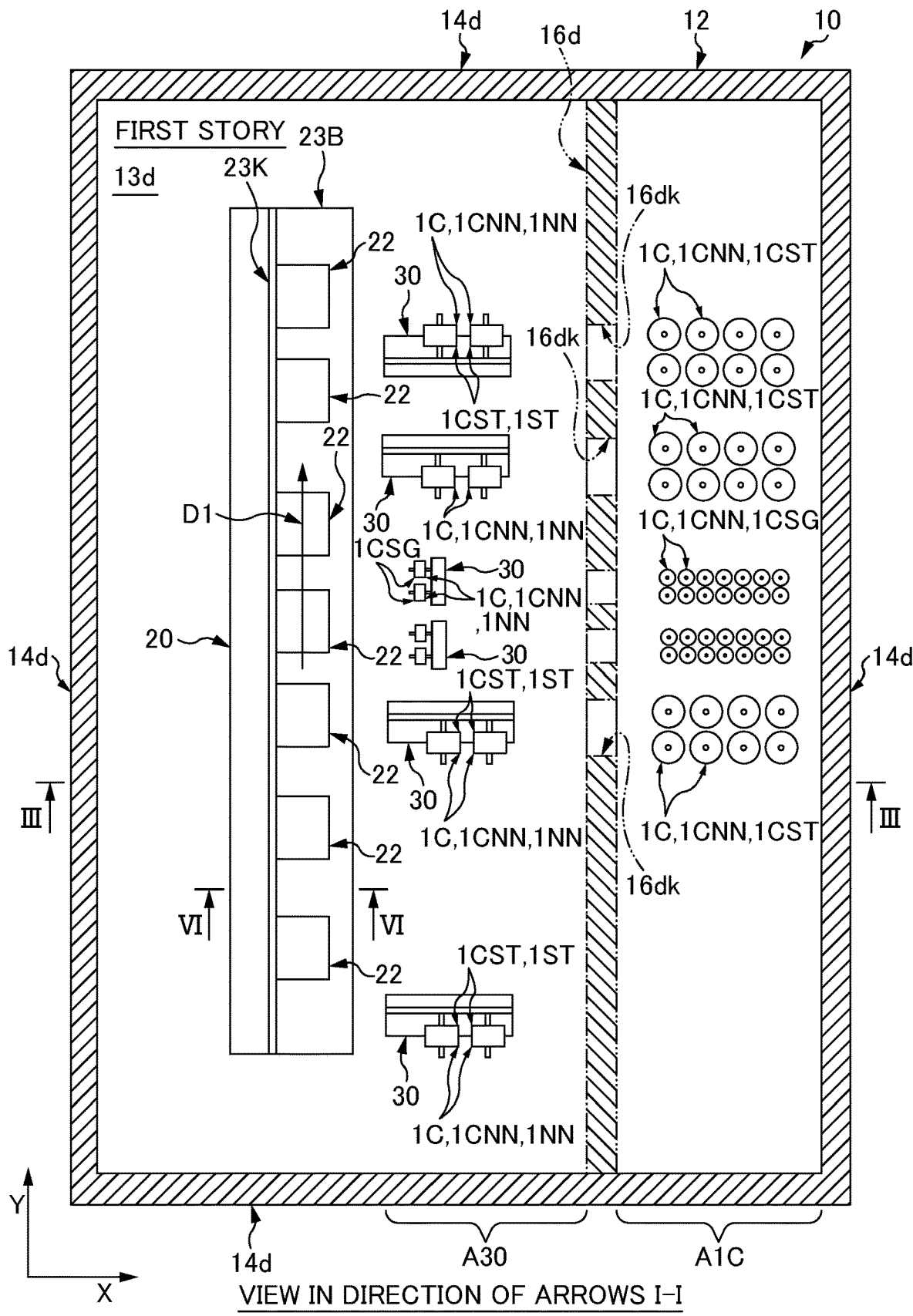
FIG. 1 is a schematic plan view of a first story of a factory 10 for manufacturing an absorbent article according to the present embodiment as viewed from above.

At least the following matters will become clear with the description of this specification and the attached drawings.

A factory for manufacturing an absorbent article by using a plurality of types of materials, including:
a building including: an upper story; and a lower story located below the upper story,
the upper story including: a floor; a wall provided along an entire periphery of the floor; an illumination device provided on a ceiling; and an air conditioner having an air outlet for discharging air,
the lower story including: a floor; a wall provided along an entire periphery of the floor; an illumination device provided on a ceiling; and an air conditioner having an air outlet for discharging air,
an opening through which the upper story and the lower story communicate being formed in the floor of the upper story,
the upper story further including a paying-out device to which a material coil on which a nonwoven fabric is wound is attached and that pays out the nonwoven fabric,
the nonwoven fabric serving as at least one type among the plurality of types of materials,
the lower story further including a processing section that processes the plurality of types of materials including the nonwoven fabric that is transported from the upper story through the opening.

With the factory for manufacturing an absorbent article, on the upper story, lint may be scattered when at least the paying-out device pays out the nonwoven fabric from the material coil. In this respect, the upper story has the floor and the wall provided along the entire periphery of the floor. That is, the upper story is surrounded by the floor of the upper story and the wall of the upper story, and accordingly the upper story is substantially isolated from the lower story. Thus, it is possible to effectively suppress lint that is scattered from the nonwoven fabric when the nonwoven fabric is paid out on the upper story from entering the lower story. Accordingly, it is possible to effectively suppress contamination due to lint adhering to another material, which may occur if lint is suspended in the air on the lower story that has the processing section.

In such a factory for manufacturing an absorbent article, it is desirable
that all types of nonwoven fabrics that the plurality of types of materials include besides the nonwoven fabric are respectively brought into the building in forms of material coils in which the nonwoven fabrics are wound, and
that paying-out devices respectively corresponding to all of the types of nonwoven fabrics are provided on the upper story to,
the paying-out devices paying out the corresponding nonwoven fabrics from the material coils.

With the factory for manufacturing an absorbent article, the material coils of all types of nonwoven fabrics that are used for manufacturing an absorbent article are paid out by the paying-out devices on the upper story. This suppresses entering, into the lower story, of lint which is scattered from all types of nonwoven fabrics when the nonwoven fabrics are paid out. Accordingly, it is possible to effectively suppress contamination due to lint adhering to another material on the lower story.

In such a factory for manufacturing an absorbent article, it is desirable
that the lower story further includes a paying-out device to which a material coil on which a non-nonwoven-fabric material is wound is attached and that pays out the non-nonwoven-fabric material, and
that the non-nonwoven-fabric material is a material that is not a nonwoven fabric, and serves as at least one type among the plurality of types of materials.

With the factory for manufacturing an absorbent article, the non-nonwoven-fabric material serving as at least one type among the plurality of types of materials is paid out from the material coil on the lower story and is transported to the processing section on the lower story. Thus, the transport distance over which the non-nonwoven-fabric material is transported to the processing section can be shortened, and accordingly it is possible to effectively prevent contamination due to lint adhering to the non-nonwoven-fabric material.

In such a factory for manufacturing an absorbent article, it is desirable
that the plurality of types of materials are respectively brought into the building in forms of material coils in which the materials are wound,
that the material coils are attached to paying-out devices that respectively correspond to the plurality of types of materials,
that the materials are paid out from the material coils, and
that among the material coils of the plurality of types of materials,
a material coil to be paid out by the paying-out device on the upper story is stored in a storage area on the upper story, and
a material coil to be paid out by the paying-out device on the lower story is stored in a storage area on the lower story.

With the factory for manufacturing an absorbent article, the material coil of a material that is paid out by the paying-out device on the lower story is stored in the storage area on the lower story. Thus, reliably suppressed is adhesion of lint that is scattered from the nonwoven fabric paid out on the upper story to the material coil on the lower story. Thus, it is possible to reliably prevent the occurrence of a problem of a material to be paid out by the paying-out device on the lower story being contaminated with lint when the material is still in a state of the material coil.

In such a factory for manufacturing an absorbent article, it is desirable
that a wall is provided between a paying-out area in which the paying-out device is provided on the upper story and the storage area on the upper story, and
that a wall is provided between a paying-out area in which the paying-out device is provided on the lower story and the storage area on the lower story.

With the factory for manufacturing an absorbent article, the wall is provided between the paying-out area and the storage area on the upper story. Thus, concerning lint which is scattered when the nonwoven fabric is paid out by the paying-out device in the paying-out area on the upper story, it is possible to effectively suppress the occurrence of a problem of the lint adhering to another material coil stored in the storage area on the upper story and contaminating the other material coil.

Likewise, the wall is provided between the paying-out area and the storage area on the lower story. Thus, concerning lint which is scattered from the nonwoven fabric, even if a nonwoven fabric is paid out by the paying-out device in the paying-out area on the lower story, it is possible to effectively suppress the occurrence of a problem of the lint adhering to another material coil stored in the storage area on the lower story and contaminating the other material coil.

In such a factory for manufacturing an absorbent article, it is desirable that a transport roller that the nonwoven fabric paid out from the material coil by the paying-out device on the upper story first comes into contact with is located on the upper story, and that a contact surface of the nonwoven fabric that comes into contact with the transport roller is a non-abutting surface that does not abut a support surface of a support member when constituent fibers of the nonwoven fabric are sucked onto and deposited on the support surface to produce the nonwoven fabric.

With the factory for manufacturing an absorbent article, concerning constituent fibers of the nonwoven fabric that have a low bonding strength and which may become lint, it is possible for most of such constituent fibers to come off and to be scattered, at the transport roller on the upper story that the nonwoven fabric first comes into contact with. Thus, it is possible to reduce the amount of lint scattered from the nonwoven fabric on the lower story after the nonwoven fabric has been transported to the lower story. Thus, it is possible to effectively prevent contamination of the lower story with lint.

The surface of the nonwoven fabric opposite to the abutting surface of the nonwoven fabric that abuts the support surface comes into contact with the transport roller, and this also effectively contributes to scattering most of the lint at the transport roller. Details are as follows.

First, basically, if the bonding strength of the constituent fibers of the nonwoven fabric at the contact surface of the nonwoven fabric that comes into contact with the transport roller is low, the fibers tend to come off the nonwoven fabric due to contact between the contact surface and the transport roller. As a result, a large amount of lint may be scattered. In a process of producing the nonwoven fabric, for generating a nonwoven fabric, when constituent fibers are sucked onto a support surface of the support member and are deposited on the support surface, the suction force more effectively acts as the distance to the support surface decreases. Thereby, the density of the fibers increases and the bonding strength of the constituent fibers tends to increase. In contrast, the density decreases and the bonding strength tends to decrease as the distance from the support surface in the direction of deposition increases. In the manufacturing method, the contact surface of the nonwoven fabric that comes into contact with the transport roller is the non-abutting surface that does not abut the support surface. Thus, the bonding strength of the constituent fibers at the contact surface that is the non-abutting surface is low, and accordingly a larger amount of fibers may come off the contact surface of the nonwoven fabric due to contact with the transport roller and may be scattered.

In such a factory for manufacturing an absorbent article, it is desirable that an air pressure at a boundary position between a space on the lower story and the opening is higher than an air pressure at a boundary position between a space on the upper story and the opening.

With the factory for manufacturing an absorbent article, the air pressure of the lower story is higher than the air pressure of the upper story. Thus, it is possible to prevent lint on the upper story from entering the lower story through the opening.

In such a factory for manufacturing an absorbent article, it is desirable that an amount ($g/m^3$) of fibers included in a unit volume at a boundary position between a space on the lower story and the opening is smaller than an amount ($g/m^3$) of fibers included in a unit volume at a boundary position between a space on the upper story and the opening.

With the factory for manufacturing an absorbent article, the amount ($g/m^3$) of fibers included in the lower story is smaller than the amount ($g/m^3$) of fibers included in the upper story. Thus, it is possible to effectively suppress contamination, with lint, of the material on the lower story that has the processing section.

In such a factory for manufacturing an absorbent article, it is desirable that when the building is viewed in cutaway from above,
the opening is disposed in such a way that at least a part of the opening overlaps the processing section.

With the factory for manufacturing an absorbent article, the opening for passing the nonwoven fabric paid out on the upper story to the lower story is disposed substantially directly above the processing section on the lower story. Thus, it is possible to shorten the transport route, on the lower story, of the nonwoven fabric transported through the opening to the lower story. Thus, it is possible to effectively prevent a problem that may occur if the transport route to the processing section on the lower story is long, that is, a problem of a large amount of lint being scattered to the lower story from the nonwoven fabric while the nonwoven fabric is transported along the long transport route and contaminating the lower story.

In such a factory for manufacturing an absorbent article, it is desirable that when the building is viewed in cutaway from above,
the paying-out device that pays out the nonwoven fabric is disposed in such a way that at least a part of the paying-out device overlaps the processing section.

With the factory for manufacturing an absorbent article, on the upper story, the paying-out device for the nonwoven fabric is disposed substantially directly above the processing section. Thus, it is possible to reduce the planar size of the entirety of the building.

In such a factory for manufacturing an absorbent article, it is desirable that in a case
where the nonwoven fabric is defined as a first nonwoven fabric,
where the material coil on which the nonwoven fabric is wound is defined as a first material coil, and
where the paying-out device for the nonwoven fabric is defined as a first paying-out device,
the plurality of types of materials include a second nonwoven fabric that is different from the first nonwoven fabric,
the upper story further includes a second paying-out device to which a second material coil on which the second nonwoven fabric is wound is attached and that pays out the second nonwoven fabric,
the first paying-out device includes:
a paying-out rotation shaft to which the first material coil that is a preceding first material coil is attached; and
a paying-out rotation shaft to which the first material coil that is a succeeding first material coil is attached,
the first paying-out device has a material splicing function of splicing the first nonwoven fabric of the succeeding first material coil with the first nonwoven fabric of the preceding first material coil in a state in which rotation of the paying-out rotation shaft to which the preceding first material coil is attached and rotation of the paying-out rotation shaft to which the succeeding first material coil is attached are both stopped, the first nonwoven fabric are accumulated in a form of a plurality of loops using a plurality of rollers that are disposed on the upper story between the first paying-out device and the processing section, while rotation of the paying-out rotation shafts is stopped, the first nonwoven fabric is supplied to the processing section by reducing sizes of the plurality of loops of the first nonwoven fabric, the second paying-out device includes:

a paying-out rotation shaft to which the second material coil that is a preceding second material coil is attached; and a paying-out rotation shaft to which the second material coil that is a succeeding second material coil is attached, and the second paying-out device has a material splicing function of splicing the second nonwoven fabric of the succeeding second material coil with the second nonwoven fabric of the preceding second material coil in a state in which the paying-out rotation shaft to which the preceding second material coil is attached and the paying-out rotation shaft to which the succeeding second material coil is attached both rotate.

With the factory for manufacturing an absorbent article, it is possible to cause most of the lint of the first nonwoven fabric to be scattered in the upper story. Thus, it is possible to effectively prevent the first nonwoven fabric from scattering lint in the lower story. Details are as follows. As described above, the first nonwoven fabric forms the plurality of loops using the plurality of rollers. The first nonwoven fabric comes into contact with the plurality of rollers in the upper story. Therefore, constituent fibers that should come off the first nonwoven fabric come off when coming into contact with the rollers and are scattered as lint. As a result, after passing through the plurality of rollers, the first nonwoven fabric has substantially no fibers that are likely to come off. Thus, after the first nonwoven fabric is transported to the lower story, scattering of lint from the first nonwoven fabric is effectively suppressed.

Present Embodiment

Figure 2:
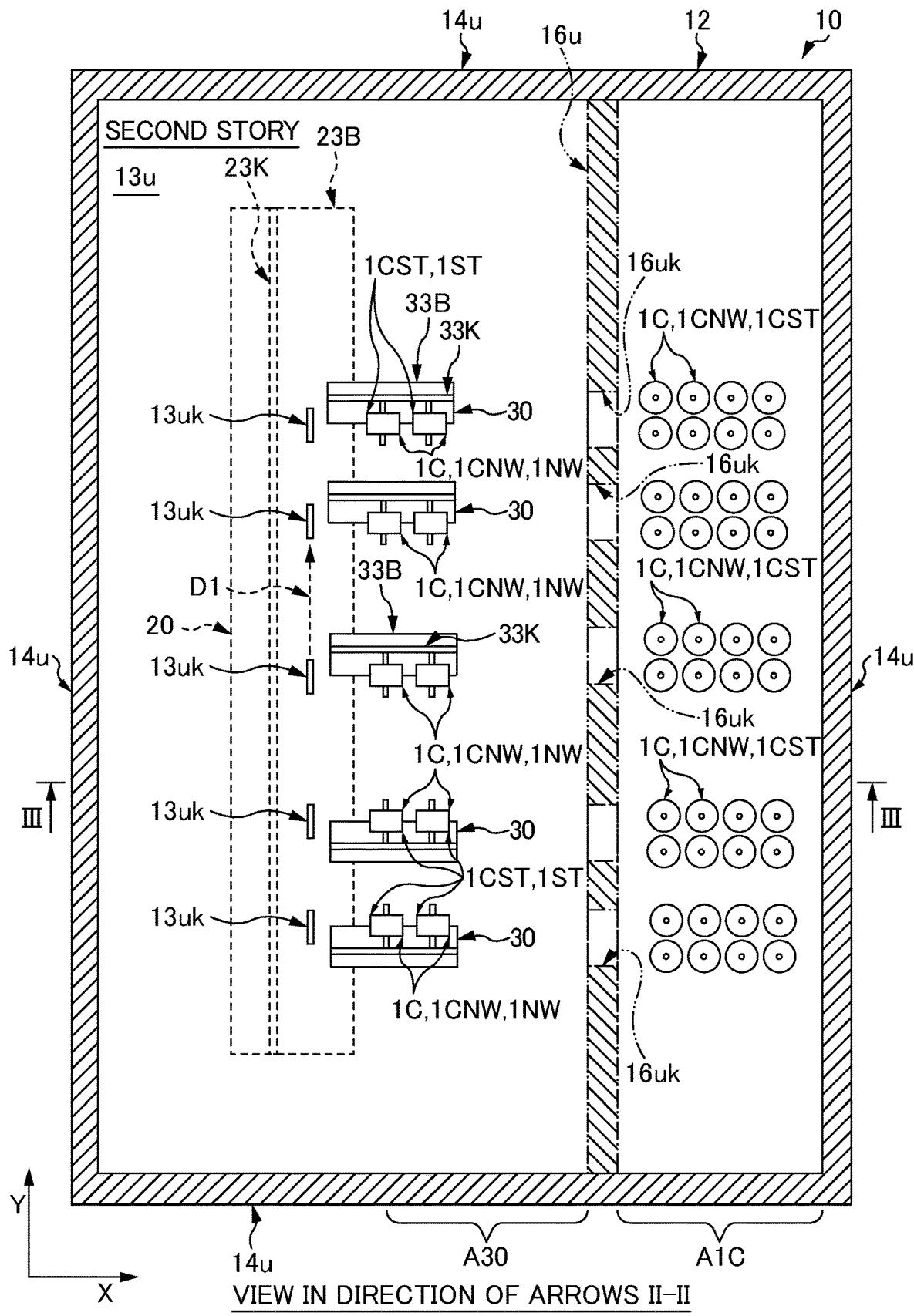
FIG. 2 is a schematic plan view of a second story as viewed from above.
Figure 3:
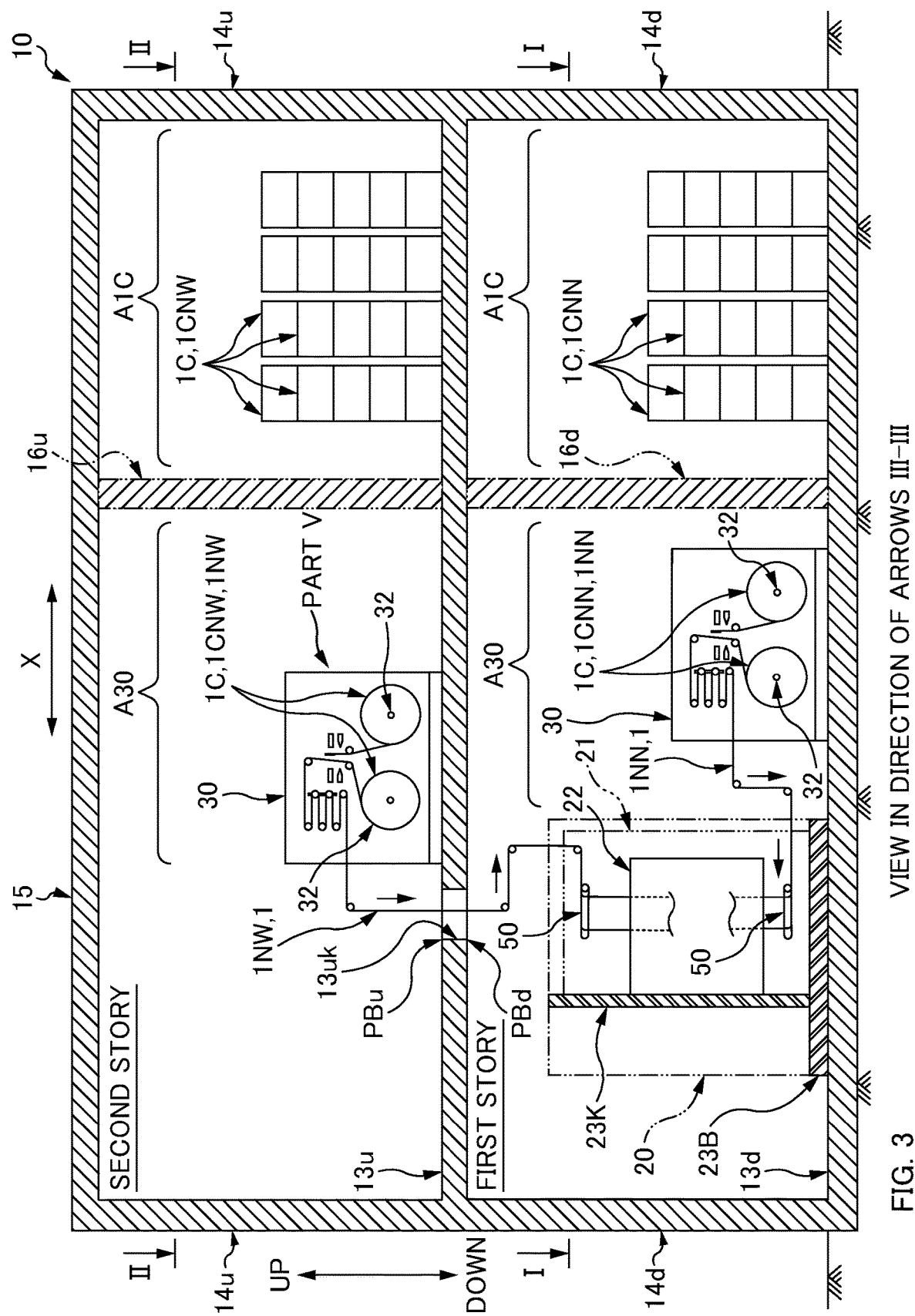
FIG. 3 is a view in the direction of arrows III-III in FIGS. 1 and 2.

FIG. 1 is a schematic plan view of a first story of a factory 10 for manufacturing an absorbent article according to the present embodiment as viewed from above. FIG. 2 is a schematic plan view of a second story of the factory 10 as viewed from above. FIG. 3 is a view in the direction of arrows III-III in FIGS. 1 and 2. FIGS. 1 and 2 are also views respectively in the directions of arrows I-I and arrows II-II in FIG. 3.

In the factory 10 for manufacturing an absorbent article, an absorbent article is manufactured by using a plurality of types of materials 1. Examples of the absorbent article include a tape-type disposable diaper, a pull-on disposable diaper, a sanitary napkin, and an incontinence pad. However, the absorbent article is not limited to any of these, provided that the absorbent article can absorb bodily waste of a wearer. As the plurality of types of materials 1, a continuous body 1NW of nonwoven fabric (hereafter, simply referred to as a nonwoven fabric 1NW), a continuous body of film (hereafter, simply referred to as film), a continuous body of tape (hereafter, simply referred to as tape), a continuous body of tissue (hereafter, simply referred to as tissue), and a continuous body of elastic string such as rubber string (hereafter, simply referred to as elastic string), and the like are used. Since the nonwoven fabric 1NW, film, tape, and elastic string can each be classified into types, the materials 1 of these types are further prepared and used.

As illustrated in FIG. 3, the factory 10 has a building 12 that has two full stories on or above the ground as an example of a plurality of stories and that is constructed with a reinforced concrete structure, a steel structure, a steel-reinforced concrete structure, or the like. The building 12 is built on a foundation (not shown) such as a mat foundation or a pile foundation. The first story as a lower story has a floor 13d and walls 14d that are provided along the entire periphery of the floor 13d. The second story as an upper story has a floor 13u and walls 14u that are provided along the entire periphery of the floor 13u. In the example illustrated in FIGS. 1 and 2, the planar shape of each of the floors 13d and 13u of the first story and the second story as viewed from above is rectangular. Therefore, the walls 14d are respectively provided on the four sides of the floor 13d of the first story. Likewise, the walls 14u are respectively provided on the four sides of the floor 13u of the second story. Thus, the second story is surrounded by the floor 13u of the second story and the four walls 14u of the second story. As a result, the second story is substantially isolated from the first story.

As illustrated in FIG. 3, the building 12 has a roof 15, and the roof 15 also functions as the ceiling of the second story. The floor 13u of the second story also functions as the ceiling of the first story. That is, the floor 13u of the second story is connected to the four walls 14d of the first story at the four sides thereof. Appropriate illumination devices (not shown), such as LED illumination devices, are discretely disposed on the ceilings of the first story and the second story to illuminate the respective stories.

Air outlets (not shown) of air conditioners are provided at appropriate positions on the first story and the second story. By discharging air from the air outlets, the air pressures (Pa) of the first story and the second story are each maintained at a positive pressure that is higher than the air pressure outside the building 12. As a result, flow of external air into the building 12 is suppressed, so that entry of bugs, dust, and the like into the building 12 can be prevented.

At least one of the four walls 14d of the first story may have a door (not shown) as an entry/exit opening of the building 12. A wall of the first story and a wall of the second story may each have a window (not shown). Moreover, a staircase (not shown) that connects the first story and the second story may be provided in the building 12. Alternatively, an exterior staircase that connects the first story and the second story may be provided outside of the building 12. In the latter case, a door is provided in at least one of the four walls 14u of the second story to correspond to the exterior staircase.

The floor 13u and the roof 15 of the second story may be supported by columns and beams (not shown) provided on each of the stories. Alternatively, the walls 14d and 14u of the first story and the second story may function as building frames, and the floor 13u and the roof 15 may be supported by the walls 14d and 14u.

As illustrated in FIGS. 1 and 3, a processing section 20 that substantially manufactures an absorbent article by using the plurality of types of materials 1 is provided on the first story of the building 12. That is, the processing section 20 processes the plurality of types of materials 1 while transporting the materials 1 in a flow direction D1. To be more specific, the plurality of types of materials 1 are respectively paid out by corresponding paying-out devices 30 described below, and the materials 1 of various types that are paid out are joined in the processing section 20 and are transported in the flow direction D1. While being transported in the flow direction D1, processing devices 22 of various types perform various processing operations, such as pressing, cutting, and joining, on the materials 1 of various types; the materials 1 are superposed on other materials 1; and finally an absorbent article is manufactured.

Examples of the processing devices 22 include a known welding device that welds the materials 1 to each other, a known pressing device that presses the material 1, and a known cutting device that cuts a part or the entirety of the material 1.

The processing section 20 on the first story may have a protective cover 21 as imaginarily shown by a three-dot chain line in FIG. 3. In this case, the protective cover 21 is disposed along the entire length of the processing section 20 in the flow direction D1. Thus, in a substantially enclosed space in the protective cover 21, the processing devices 22 of the processing section 20 process the materials 1 of various types that are transported in the flow direction D1. The reason for providing the protective cover 21 on the first story is that operators enter the first story more frequently than the second story to, for example, monitor the operating states of the processing devices 22 provided on the first story. The protective cover 21 may have doors at positions that face the processing devices 22 in the flow direction D1. In this case, an operator can quickly access the processing device 22 by opening the door when any of the processing devices 22 causes a problem, thereby shortening the recovery time of the device 22.

Hereafter, for convenience of description, two horizontal directions that are perpendicular to the vertical direction and that are perpendicular to each other will be referred to as the "X-direction" and the "Y-direction", as illustrated in FIG. 1. In this example, the flow direction D1 is the Y-direction in plan view.

The materials 1 of various types are respectively brought into the building 12 in the form of material coils 1C in which the materials 1 are wound. Therefore, as illustrated in FIGS. 1 to 3, a paying-out area A30 in which the materials 1 are paid out from the material coils 1C is provided in the building 12. That is, the paying-out devices 30 are provided in the paying-out area A30 to respectively correspond to the types of the materials 1. The material coils 1C for these types of the materials 1 are attached to the corresponding paying-out devices 30 and are paid out. The paying-out area A30 is provided on each of the first story and the second story.

As illustrated in FIG. 1, the paying-out area A30 on the first story is an elongated region extending in the flow direction D1 of the processing section 20. That is, on the first story, a plurality of paying-out devices 30 are arranged in the flow direction D1. The materials 1 paid out by the paying-out devices 30 are transported to the processing section 20 on the first story.

The paying-out area A30 on the second story, which is illustrated in FIG. 2, is also an elongated region extending in the flow direction D1 of the processing section 20. That is, also on the second story, a plurality of paying-out devices 30 are arranged in the flow direction D1. The materials 1 of various types paid out by the paying-out devices 30 are transported to the processing section on the first story through communication openings 13$uk$ (each corresponding to an opening, refer also to FIG. 3); each of the communication openings 13$uk$ has a substantially rectangular shape in plan view and is provided in the floor 13$u$ of the second story to communicate with the first story. As illustrated in FIG. 2, the communication openings 13$uk$ are formed respectively for the paying-out devices 30, and accordingly only one type of material 1 passes through each communication opening 13$uk$.

In the present embodiment, the paying-out device 30 for at least one type of nonwoven fabric 1NW among all types of nonwoven fabrics 1NW that are used in the factory 10 is disposed in the paying-out area A30 on the second story illustrated FIG. 2. To be precise, the paying-out devices 30 for a half or more of all types of nonwoven fabrics 1NW are disposed on the second story. To be more precise, the paying-out devices 30 for all types of nonwoven fabrics 1NW are disposed on the second story. When a material 1 that is not a nonwoven fabric 1NW is referred to as a "non-nonwoven-fabric material 1NN", in the paying-out area A30 on the first story illustrated in FIG. 1, disposed is the paying-out device 30 for at least one type of non-nonwoven-fabric material 1NN among all types of non-nonwoven-fabric materials 1NN that are used in the factory 10. To be precise, the paying-out devices 30 for a half or more of all types of non-nonwoven-fabric materials 1NN are disposed on the first story. To be more precise, the paying-out devices 30 for all types of non-nonwoven-fabric materials 1NN are disposed on the first story.

Thus, it is possible to suppress the occurrence of the problem described at the beginning, that is, the problem of "lint of a nonwoven fabric 1NW adhering to a non-nonwoven-fabric material 1NN on the first story that has the processing section 20 and contaminating the non-nonwoven-fabric material 1NN". Details are as follows. First, on the second story illustrated in FIGS. 2 and 3, lint may be scattered when the paying-out device 30 for the nonwoven fabric 1NW pays out the nonwoven fabric 1NW from a material coil 1CNW (1C). However, in this respect, the second story has the floor 13$u$ and the walls 14$u$ that are provided along the entire periphery of the floor 13$u$. That is, the second story is surrounded by the floor 13$u$ of the second story and the four walls 14$u$ of the second story, thereby substantially isolating the second story from the first story. Therefore, it is possible to effectively suppress lint that is scattered from the nonwoven fabric 1NW when the nonwoven fabric 1NW is paid out on the second story from entering the first story. Thus, it is possible to effectively suppress contamination due to lint adhering to the non-nonwoven-fabric material 1NN, which may occur if lint is suspended in the air on the first story that has the processing section 20.

As illustrated in FIG. 3, all types of non-nonwoven-fabric materials 1NN are paid out from material coils 1CNN (1C) by the paying-out devices 30 in the paying-out area A30 on the first story and transported to the processing section 20 on the first story. Thus, the transport distance over which the non-nonwoven-fabric material 1NN is transported to the processing section 20 can be shortened, and accordingly it is possible to effectively suppress contamination due to lint adhering to the non-nonwoven-fabric material 1NN on the first story.

However, this is not a limitation. For example, supposing the case where the layout of devices in the building 12 is prioritized and a slight reduction of the effect of suppressing contamination with lint does not pose a serious problem. In this case, one type or some, but not all, of the types of nonwoven fabrics 1NW may be paid out by the paying-out device(s) 30 in the paying-out area A30 on the first story illustrated in FIG. 1, or one type or some, but not all, of the types of non-nonwoven-fabrics 1NN may be paid out by the paying-out device(s) 30 in the paying-out area A30 on the second story illustrated in FIG. 2.

In this example, a material 1 corresponding to the non-nonwoven-fabric material 1NN is any of the film, the tape, the elastic string, and the tissue, which are mentioned above, and the like. That is, in a narrow sense, the term "nonwoven fabric 1NW" refers to a nonwoven fabric composed of thermoplastic resin fibers such as polyester fibers or polypropylene fibers. In a broad sense, the term "nonwoven fabric 1NW" refers to a nonwoven fabric-like sheet.

Until a material coil 1C brought into the building 12 is attached to a paying-out device 30, the material coil 1C is stored in the storage area A1C in the building 12. The storage area A1C is provided on each of the first story and the second story. To be specific, as illustrated in FIG. 1, the storage area A1C on the first story is provided adjacent to the paying-out area A30 on the first story. As illustrated in FIG. 2, the storage area A1C on the second story is provided adjacent to the paying-out area A30 on the second story. The material coils 1C (1CNN) to be paid out by the paying-out devices 30 on the first story are stored in the storage area A1C on the first story. The material coils 1C (1CNW) to be paid out by the paying-out devices 30 on the second story are stored in the storage area A1C on the second story.

Thus, reliably suppressed is adhesion of lint that is scattered from the nonwoven fabric 1NW paid out on the second story to the material coil 1CNN of the non-nonwoven-fabric material 1NN stored on the first story. Thus, it is possible to reliably prevent the occurrence of a problem of the non-nonwoven-fabric material 1NN to be paid out by the paying-out device 30 on the first story being contaminated with lint when the non-nonwoven-fabric material 1NN is still in a state of the material coil 1CNN.

Preferably, as shown by a two-dot chain line in FIGS. 2 and 3, a wall 16$u$ is provided between the paying-out area A30 on the second story and the storage area A1C on the second story, thereby separating the areas A30 and A1C from each other. In this case, concerning lint which is scattered from the nonwoven fabric 1NW when the paying-out device 30 in the paying-out area A30 on the second story pays out the nonwoven fabric 1NW, it is possible to effectively suppress the occurrence of a problem of the lint adhering to the material coil 1C (1CNW) stored in the storage area A1C on the second story and contaminating it. Likewise, preferably, as shown by a two-dot chain line in FIGS. 1 and 3, a wall 16$d$ is provided between the paying-out area A30 on the first story and the storage area A1C on the first story, thereby separating the areas A30 and A1C from each other. In this case, concerning lint which is scattered from the nonwoven fabric 1NW, even if the paying-out device 30 in the paying-out area A30 on the first story pays out the nonwoven fabric 1NW as the material 1, it is possible to effectively suppress the occurrence of a problem of the lint adhering to the material coil 1C (1CNN) stored in the storage area A1C on the first story and contaminating it.

If the material coil 1C is to be brought from the storage area A1C into the paying-out area A30 via the walls 16$d$ and 16$u$, preferably, as illustrated in FIGS. 1 and 2, openings 16$dk$ and 16$uk$ are respectively formed in parts of the walls 16$d$ and 16$u$, as communication openings for bringing coils in.

Preferably, the air pressure (Pa) at a boundary position PBd between the space on the first story and the communication opening 13$uk$ shown in FIG. 3 is higher than the air pressure (Pa) at a boundary position PBu between the space on the second story and the communication opening 13$uk$. In this case, it is possible to effectively prevent lint from the second story from entering the first story through the communication opening 13$uk$.

It is possible to make the air pressure of the first story higher than the air pressure of the second story by, for example, making the amount per unit time (m$^3$/s) of air that is discharged from the air outlet (not shown) of the air conditioner on the first story be larger than the amount per unit time (m$^3$/s) of air that is discharged from the air outlet (not shown) of the air conditioner on the second story. The air conditioner is exemplified by an air conditioner including: such an air outlet at the downstream end in the airflow direction; a duct that is capable of sucking both outdoor air and air inside the building 12; and a blower fan that moves air inside the duct toward the air outlet.

Suppose that each of the air conditioners on the first story and the air conditioner on the second story has a function of cleaning air, that is, that each of the air conditioners has an appropriate cleaning filter in the flow path in the duct so that the air conditioner can clean air sucked thereinto and can blow the air from the air outlet. In such a case, the cleanliness of air on the first story may be set larger than the cleanliness of air on the second story by, for example, selection of the fineness of the meshes of the cleaning filter. To be specific, the amount (g/m$^3$) of fibers included in a unit volume at the boundary position PBd between the space on the first story and the communication opening 13$uk$ illustrated in FIG. 3 may be set smaller than the amount (g/m$^3$) of fibers included in a unit volume at the boundary position PBu between the space on the second story and the communication opening 13$uk$. In this case, it is possible to effectively suppress contamination, with lint, of the material 1 (1NN) on the first story that has the processing section 20.

The paying-out devices 30 are roughly classified into two types with respect to the paying-out method. That is, the paying-out devices 30 are roughly classified as a paying-out device 30 that pays out a string-shaped material 1SG such as an elastic string, and a paying-out device 30 that pays out a sheet-shaped material 1ST such as a nonwoven fabric, a film, or a tape.

Figure 4:
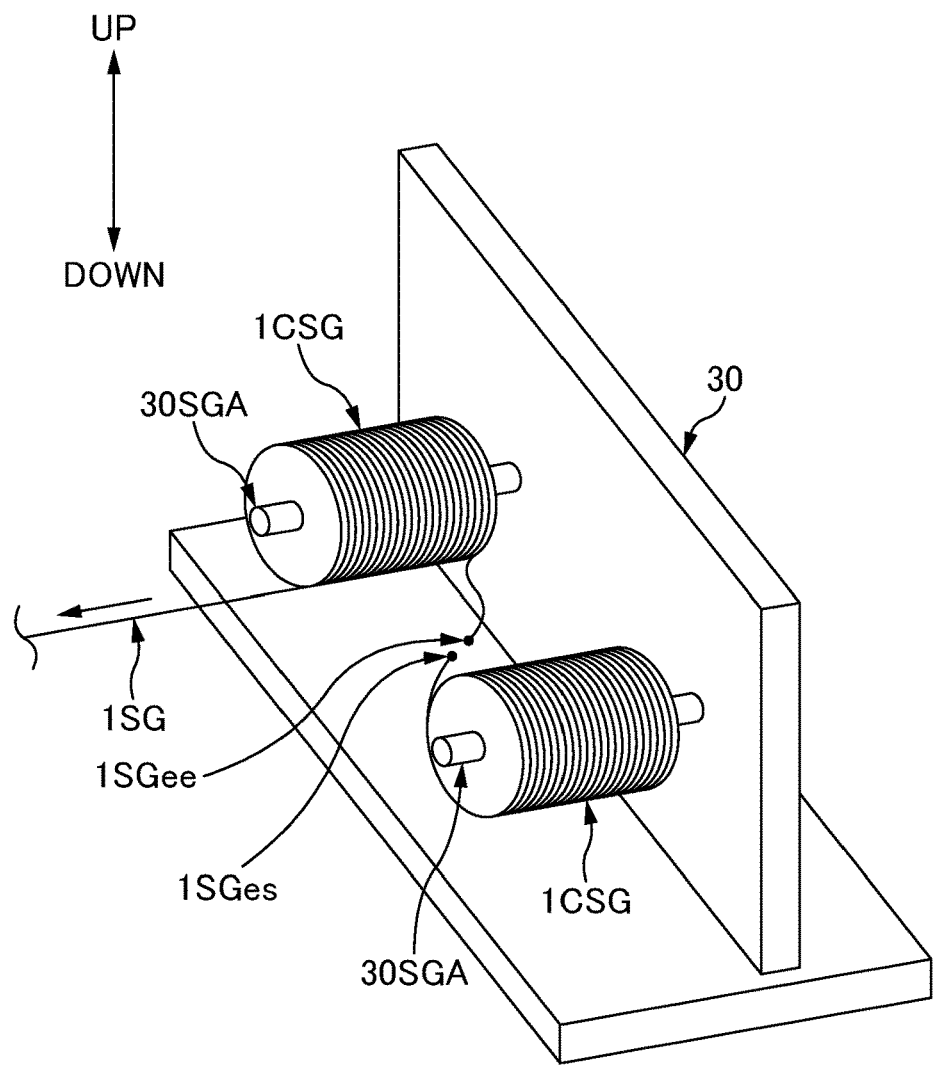
FIG. 4 is a schematic perspective view of a paying-out device 30 for a string-shaped material 1SG.

FIG. 4 is a schematic perspective view of the former paying-out device 30 for paying out the string-shaped material 1SG. The paying-out device 30 pays out the string-shaped material 1SG by using, for example, an over-end unwinding (over-end take-off) method. That is, a material coil 1CSG, in which the string-shaped material 1SG is wound, is unrotatably and coaxially attached to an unrotatable support shaft 30SGA for supporting the material coil 1CSG. Then, as the string-shaped material 1SG is pulled in the axial direction of the material coil 1CSG, the string-shaped material 1SG is successively paid out from the unrotatable material coil 1CSG. As a result, the string-shaped material 1SG is transported to the processing section 20.

When the string-shaped material 1SG is paid out, the material coil 1CSG does not rotate around the axis thereof as described above. Therefore, by connecting in advance a leading end 1SGes of a succeeding material coil 1CSG to a trailing end 1SGee of the string-shaped material 1SG of a preceding material coil 1CSG that is being paid out, before the material 1SG of the preceding material coil 1CSG is depleted, a material coil to be paid out can be smoothly changed from the preceding material coil 1CSG to the succeeding material coil 1CSG without stopping paying-off.

Figure 5:
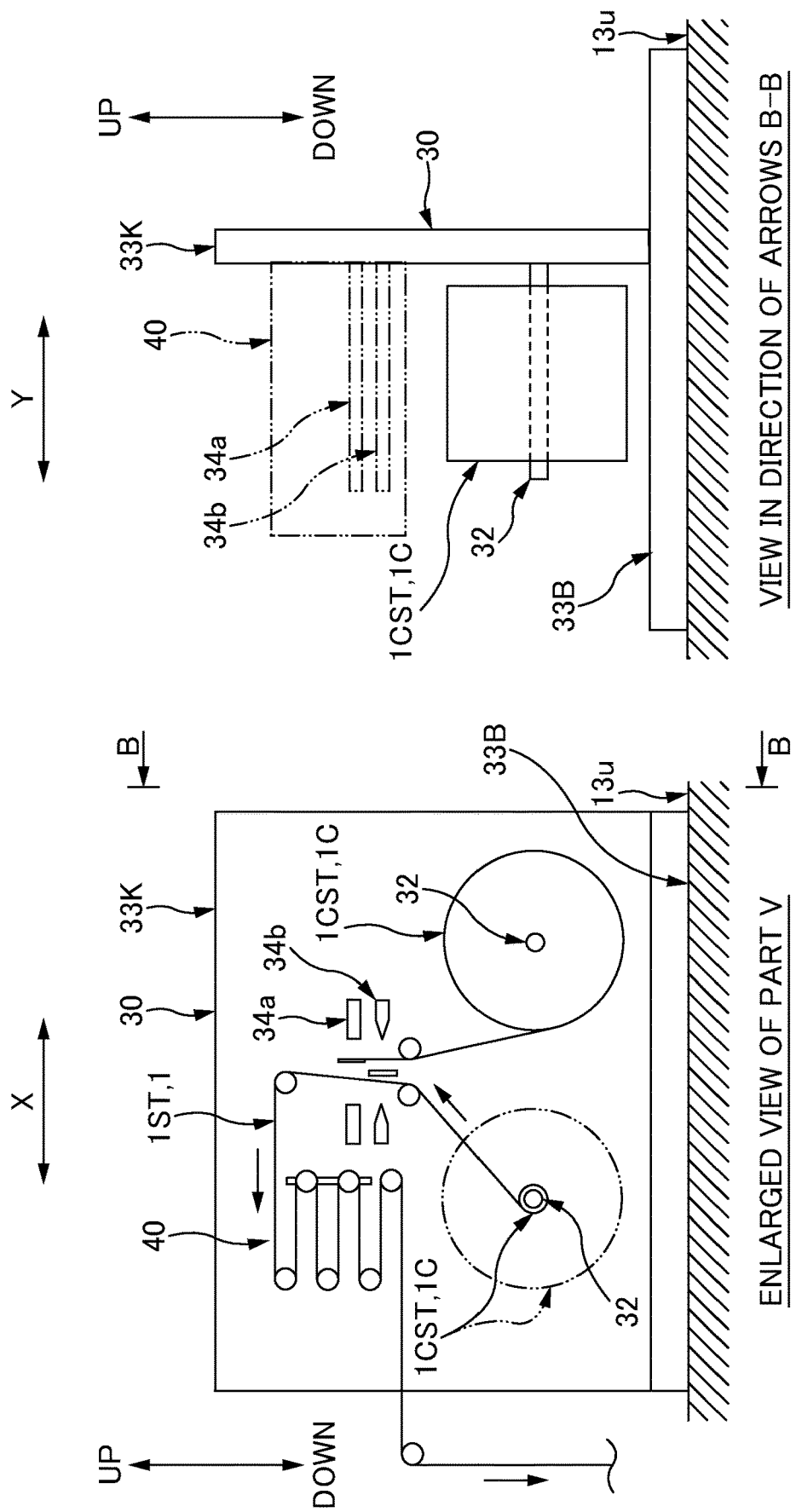
FIG. 5A is an enlarged view of part V in FIG. 3, illustrating a paying-out device 30 for a sheet-shaped material 1ST.
FIG. 5B is a view in the direction of arrows B-B in FIG. 5A.

FIGS. 5A and 5B illustrate the latter paying-out device 30 for the sheet-shaped material 1ST. FIG. 5A is a schematic enlarged view of part V of FIG. 3, and FIG. 5B is a view in the direction of arrows B-B in FIG. 5A. As described below, paying-out devices 30 of two types, which are of a type 1 and a type 2, are used as the paying-out devices 30 for the sheet-shaped material 1ST. Here, the paying-out devices 30 for the sheet-shaped material 1ST will be described with reference to the type-1 paying-out device 30 as a representative of the two types. That is, first, matters common to the type-1 and type-2 paying-out devices 30 will be described below. Then, matters characteristic of each of the type-1 and type-2 paying-out devices 30 will be described independently.

As illustrated in FIGS. 5A and 5B, the paying-out device 30 for the sheet-shaped material 1ST includes a pair of paying-out rotation shafts 32. A material coil 1CST (1C) can be attached to each of the pair of paying-out rotation shafts 32. Each of the pair of paying-out rotation shafts 32 has a motor (not shown) as a driving source, and accordingly the paying-out rotation shafts 32 can be rotated independently from each other. Thus, when one of the paying-out rotation shafts 32 is rotated, the material 1ST (1) is paid out from the material coil 1CST (1C) attached to the paying-out rotation shaft 32, and the material 1 that is paid out is transported to the processing section 20.

The paying-out device 30 also has a material splicing function of performing a material splicing operation. That is, in the material splicing operation, before the material 1ST paid out from the preceding material coil 1CST is depleted, the material 1ST of the succeeding material coil 1CST is spliced with the material 1ST of the preceding material coil 1CST. Thus, a material coil 1CST from which the material 1ST is to be paid out is changed from the preceding material coil 1CST to the succeeding material coil 1CST. The material splicing operation will be described below.

As illustrated in FIGS. 5A and 5B, the paying-out device 30 includes a base portion 33B and a plate portion 33K, as a support structure for supporting the pair of paying-out rotation shafts 32. The base portion 33B is set on the floor 13d or 13u of the first story or the second story and has a substantially rectangular plate-like shape in plan view. The plate portion 33K stands on the upper surface of the base portion 33B and has a vertical surface that is substantially rectangular in side view. The pair of paying-out rotation shafts 32 extend in a direction normal to the vertical surface of the plate portion 33K, and the paying-out rotation shafts 32 are each rotatably supported at one end thereof by the vertical surface of the plate portion 33K.

Figure 6:
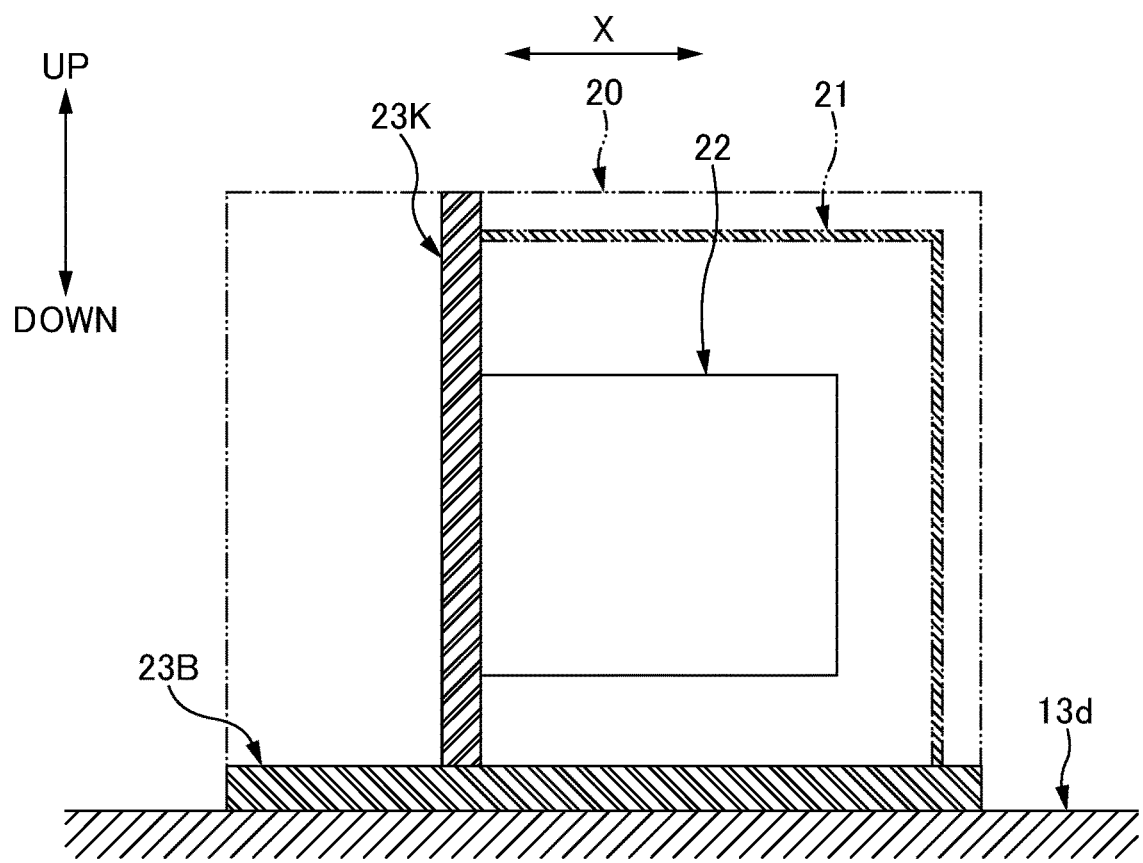
FIG. 6 is a view in the direction of arrows VI-VI in FIG. 1.

FIG. 6 is a view in the direction of arrows VI-VI in FIG. 1. Each processing device 22 of the processing section 20 is also supported by the floor 13d of the first story via a similar support structure. That is, as illustrated in FIGS. 1 and 6, the processing section 20 includes a base portion 23B and a plate portion 23K. The base portion 23B is a horizontal plate that is set on the floor 13d of the first story to extend in the Y-direction, which is the flow direction, and that has a substantially rectangular shape in plan view. The plate portion 23K stands on an upper surface of the base portion 23B, extends in the Y-direction, and has a vertical surface that is substantially rectangular in side view. Each processing device 22 is attached to and supported by the vertical surface of the plate portion 23K.

Preferably, as illustrated in FIG. 2, for each paying-out device 30 on the second story, at least one, some, or all of the communication openings 13uk in the floor 13u of the second story are arranged to have the following positional relationship with the processing section 20. That is, preferably, when the building 12 is viewed in cutaway from above as in FIG. 2, the communication opening 13uk is disposed in such a way that at least a part of the communication opening 13uk overlaps the processing section 20. In this example, the entirety of the communication opening 13uk overlaps the processing section 20.

In this case, the communication opening 13uk is disposed directly above the processing section 20. Therefore, it is possible for the nonwoven fabric 1NW transported to the first story through the communication opening 13uk to reach the processing section 20 along a comparatively short transport route on the first story. Thus, it is possible to effectively prevent a problem that may occur if the transport route to the processing section 20 on the first story is long, that is, a problem of a large amount of lint being scattered to the first story from the nonwoven fabric 1NW while the nonwoven fabric 1NW is transported along the long transport route and contaminating the first story.

Here, the expression "at least a part of the communication opening 13uk overlaps the processing section 20 as viewed from above" means that at least a part of the communication opening 13uk overlaps the base portion 23B of the processing section 20 as viewed from above. This definition is possible because processing of the nonwoven fabric 1NW is performed substantially above the base portion 23B of the processing section 20.

Preferably, as illustrated in FIG. 2, at least one, some, or all of the paying-out devices 30 for the nonwoven fabric 1NW on the second story are arranged to have the following positional relationship with the processing section 20. That is, preferably, when the building 12 is viewed in cutaway from above as in FIG. 2, the paying-out device 30 for the nonwoven fabric 1NW is disposed in such a way that at least a part of the paying-out device 30 overlaps the processing section 20.

In this case, the paying-out device 30 is disposed substantially directly above the processing section 20. Therefore, it is possible to transport the nonwoven fabric 1NW to the communication opening 13uk along a comparatively short transport route on the second story. Thus, it is possible to prevent the occurrence of a problem that tends to occur if the transport route is long, such as a problem of the nonwoven fabric 1NW that is being transported becoming stuck on a peripheral device or the like. Moreover, it is also possible to reduce the planar size of the entirety of the building 12.

Here, the expression "at least a part of the paying-out device 30 overlaps the processing section 20 as viewed from above" means that at least a part of the base portion 33B of the paying-out device 30 overlaps the base portion 23B of the processing section 20 as viewed from above. This definition is possible because paying-out of the nonwoven fabric 1NW is performed substantially above the base portion of the paying-out device 30 and because processing of the nonwoven fabric 1NW is performed above the base portion 23B of the processing section 20 as described above.

Figure 7A:
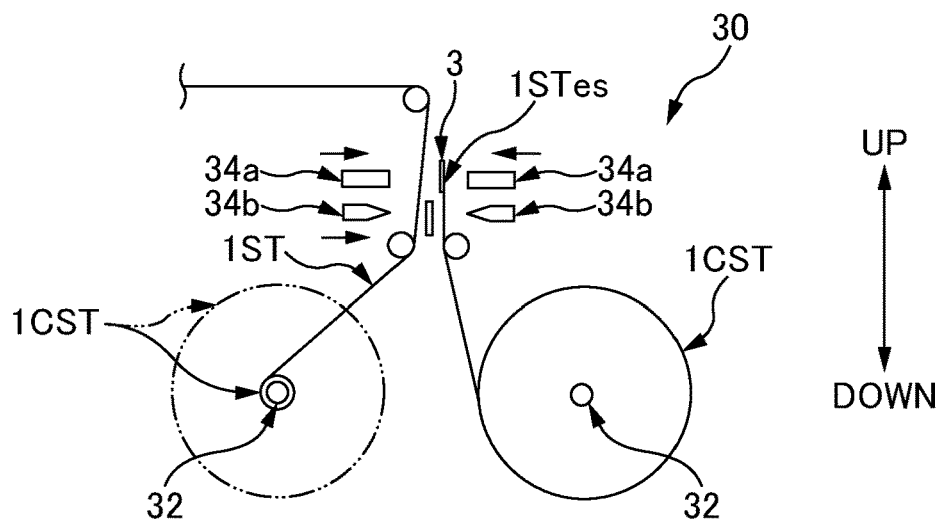
FIGS. 7A to 7C illustrate a type-1 paying-out device 30.
Figure 7B:
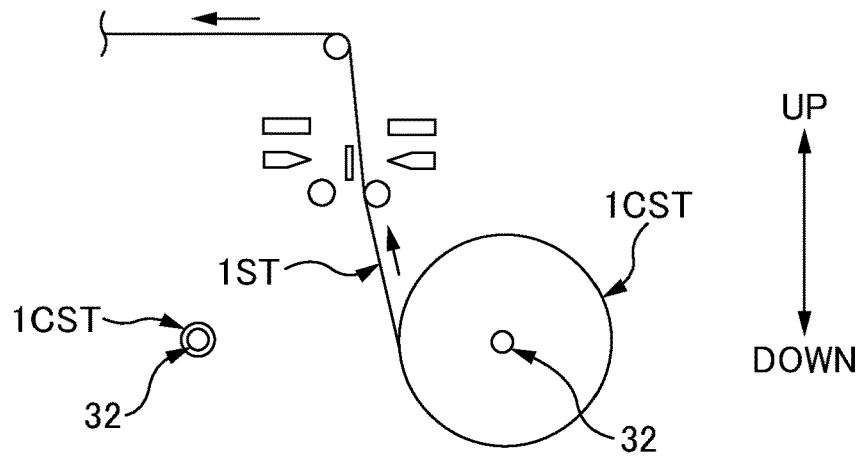
Figure 7C:
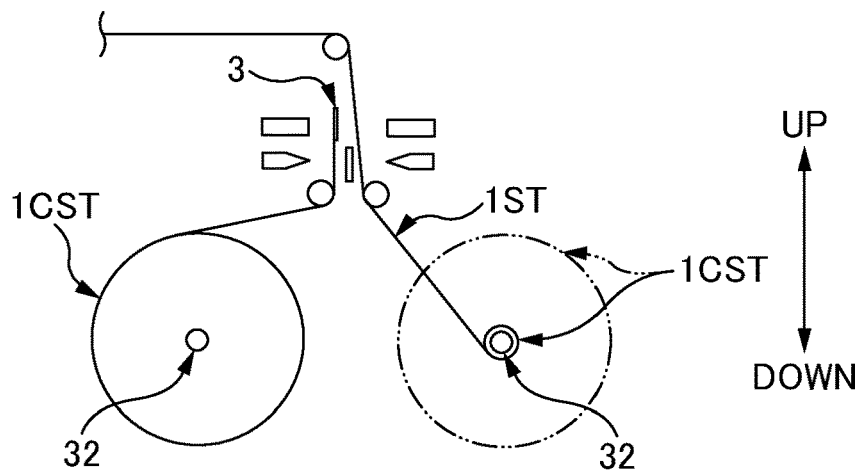

As described above, the paying-out device 30 has a material splicing function. The factory 10 has two types of paying-out devices 30 that differ from each other in material splicing method. That is, a type-1 paying-out device 30 splices the material 1ST of the succeeding material coil 1CST with the material 1ST of the preceding material coil 1CST in a state in which rotation of the preceding paying-out rotation shaft 32 and rotation of the succeeding paying-out rotation shaft 32 are both stopped (FIGS. 7A to 7C). A type-2 paying-out device 30 splices the material 1ST of the succeeding material coil 1CST with the material 1ST of the preceding material coil 1CST in a state in which the preceding paying-out rotation shaft 32 and the succeeding paying-out rotation shaft 32 both rotate (FIGS. 9A to 9C).

Referring to FIGS. 7A to 7C, first, the type-1 paying-out device 30 (corresponding to a first paying-out device) will be described.

As illustrated in FIG. 7A, a material splicing operation is started just before the material 1ST of the preceding material coil 1CST is depleted. In the material splicing operation, first, rotation of the paying-out rotation shaft 32 of the preceding material coil 1CST is stopped, thereby stopping paying-out of the material 1ST. Rotation of the paying-out rotation shaft 32 of the succeeding material coil 1CST is stopped beforehand. A leading end 1STes of the material 1ST of the succeeding material coil 1CST has been pulled out to the position of a pressing device 34a beforehand, and rotation of the succeeding material coil 1CST is stopped in this state. The pressing device 34a holds the leading end 1STes of the material 1ST of the succeeding material coil 1CST and the material 1ST of the preceding material coil 1CST together, thereby connecting the leading end 1STes to the material 1ST of the preceding material coil 1CST via a double-sided tape 3.

After the connecting step, the material 1ST of the preceding material coil 1CST is cut by a cutting device 34b. After the cutting step, the material 1ST is paid out from the succeeding material coil 1CST as illustrated in FIG. 7B. While the material 1ST is being paid out from the succeeding material coil 1CST, the preceding material coil 1CST is removed from the paying-out rotation shaft 32 as a material coil 1CST that has been paid out. Instead of the preceding material coil 1CST, as illustrated in FIG. 7C, a new material coil 1CST before being paid out is attached to the paying-out rotation shaft 32. Thus, in the subsequent material splicing operation, the succeeding material coil 1CST becomes a new preceding material coil 1CST, and the material coil 1CST before being paid out becomes a new succeeding material coil 1CST. As illustrated in FIG. 7C, just before the material 1ST of the new preceding material coil 1CST is depleted, the subsequent material splicing operation is started. The subsequent material splicing operation is performed by repeating the steps described above.

While rotation of the paying-out rotation shaft 32 of the preceding material coil 1CST is stopped as illustrated in FIG. 7A, a material accumulation device 40 (FIG. 5), which is provided between the paying-out rotation shaft 32 and the processing section 20, supplies the material 1ST that has been accumulated beforehand to the processing section 20. Thus, the processing section 20 can continuously perform an operation of processing an absorbent article without stopping the operation.

Figure 8:
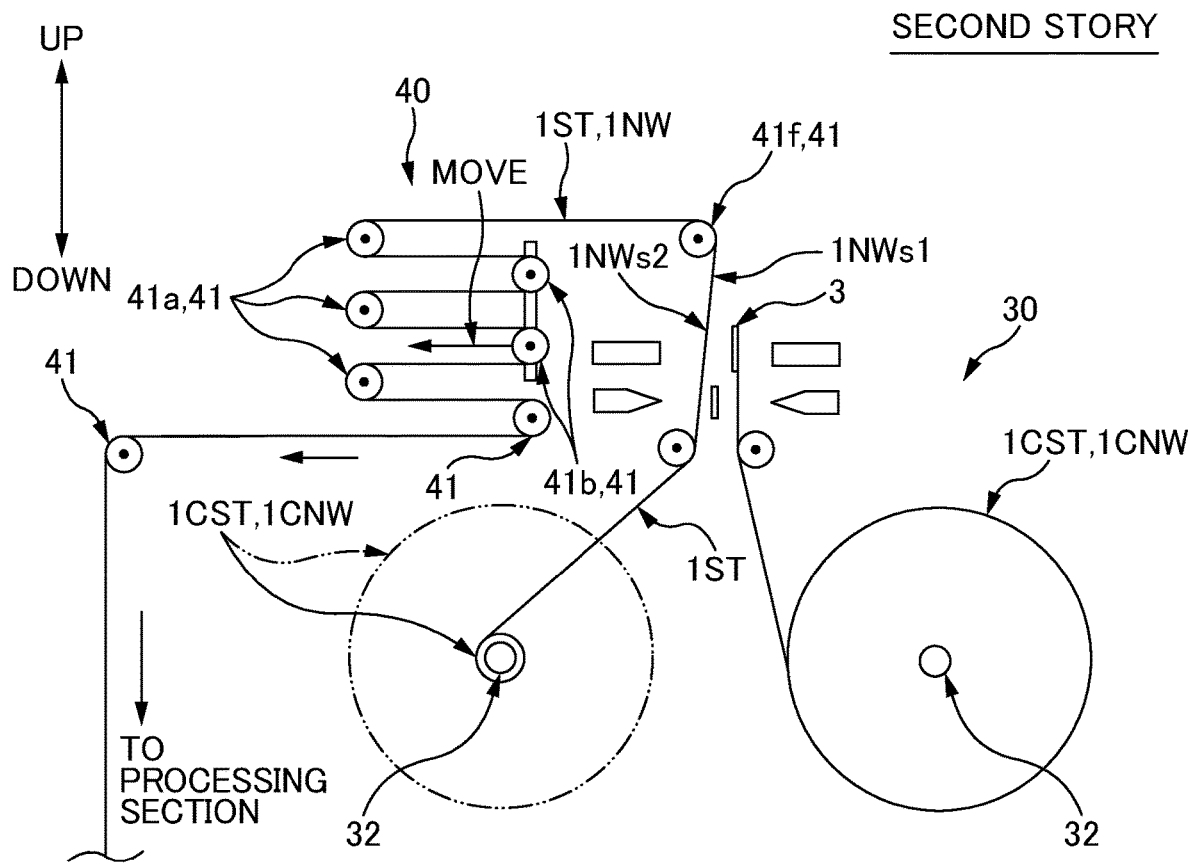
FIG. 8 illustrates a material accumulation device 40.

FIG. 8 illustrates the material accumulation device 40. The material accumulation device 40 is provided on the second story, as with the paying-out device 30. The device 40 includes: a plurality of fixed-position rollers 41a that are rotatably supported at fixed positions; and a plurality of mobile rollers 41b that are rotatably supported while being guided to be reciprocable in the horizontal direction, which is an example of a direction in which distances from the fixed-position rollers 41a can be changed. The preceding material 1ST is looped being alternately wound on the fixed-position rollers 41a and the mobile rollers 41b, forming a plurality of loops of the material 1ST. Thereby the material 1ST is accumulated in the form of a plurality of loops. Thus, while rotation of the paying-out rotation shaft 32 of the preceding material coil 1CST is stopped, the preceding material 1ST can be supplied to the processing section 20 by moving the mobile rollers 41b in the horizontal direction such that the sizes of the loops are reduced. Accumulation of the loops of the material 1ST consumed at this time is performed at an appropriate time after the material splicing operation is finished and before the subsequent material splicing operation is started.

Preferably, the type-1 paying-out devices 30 are used as at least one, some, or all of the paying-out devices 30 for the nonwoven fabric 1NW on the second story.

In this case, concerning the nonwoven fabric 1NW (corresponding to a first nonwoven fabric) of the material coil 1CNW for which the type-1 paying-out device 30 is used, it is possible to cause most of the lint of the nonwoven fabric 1NW to be scattered in the second story of the building 12. Thus, it is possible to effectively prevent the nonwoven fabric 1NW from scattering lint in the first story. Details are as follows.

As described above, the nonwoven fabric 1NW illustrated in FIG. 8 forms a plurality of loops using the plurality of rollers 41a and 41b of the material accumulation device 40. The nonwoven fabric 1NW, which is paid out by the paying-out device 30 and transported, comes into contact with the plurality of rollers 41a and 41b in the second story. Therefore, constituent fibers that should come off the nonwoven fabric 1NW come off when coming into contact with the rollers 41a and 41b and are scattered as lint. As a result, after passing through the plurality of rollers 41a and 41b, the nonwoven fabric 1NW has substantially no constituent fibers that are likely to come off. Thus, when the nonwoven fabric 1NW is transported to the first story, scattering of lint from the nonwoven fabric 1NW in the first story is effectively suppressed.

Next, referring to FIGS. 9A to 9C, the type-2 paying-out device 30 (corresponding to a second paying-out device) will be described.

As illustrated in FIG. 9A, a material splicing operation is started just before the material 1 of the preceding material coil 1CST, which is being paid out as the paying-out rotation shaft 32 rotates, is depleted. In the material splicing operation, the materials 1ST of the preceding material coil 1CST and the succeeding material coil 1CST are spliced together in a state in which the material coils 1CST are rotating at the same rotational speed (mpm).

Therefore, first, the succeeding material coil 1CST is rotated by rotating the paying-out rotation shaft 32 of the succeeding material coil 1CST, and the rotational speed of the succeeding material coil 1CST is increased to the same rotational speed (mpm) as the preceding material coil 1CST. Then, at the same time as the double-sided tape 3, which has been attached to the rotating succeeding material coil 1CST beforehand, passes the position of a roller-like pressing device 35a in the direction of rotation of the material coil 1CST, the pressing device 35a presses the leading end 1STes of succeeding material coil 1CST against the material 1ST of the preceding material coil 1CST. Thus, the leading end 1STes is connected to the material 1ST of the preceding material coil 1CST with the double-sided tape 3.

After the connecting step, the material 1ST of the preceding material coil 1CST is cut by a cutting device 35b. Subsequently, as illustrated in FIG. 9B, the material 1ST is paid out from the succeeding material coil 1CST. While the material 1ST is being paid out from the succeeding material coil 1CST, the preceding material coil 1CST is removed from the paying-out rotation shaft 32 as a material coil 1CST that has been paid out. Instead of the preceding material coil 1CST, as illustrated in FIG. 9C, a new material coil 1CST before being paid out is attached to the paying-out rotation shaft 32. Thus, in the subsequent material splicing operation, the succeeding material coil 1CST becomes a new preceding material coil 1CST, and the material coil 1CST before being paid out becomes a new succeeding material coil 1CST.

As illustrated in FIG. 9C, just before the material 1ST paid out from the new preceding material coil 1CST is depleted, this time, the material 1ST of the new succeeding material coil 1CST is spliced with the material 1ST of the new preceding material coil 1CST. Before this, a turret 45 is rotated by 180°, thereby switching the position of the new preceding material coil 1CST and the position of the new succeeding material coil 1CST as illustrated in FIG. 9A. The subsequent material splicing operation is performed by repeating the steps described above.

The paying-out devices 30 of the second type may be used as at least one, some, or all of the paying-out devices 30 for the nonwoven fabric 1NW (corresponding to a second nonwoven fabric) disposed in the paying-out area A30 on the second story. If at least one type-2 paying-out device 30 is provided in the paying-out area A30 on the second story and at least one type-1 paying-out device 30 is provided in the paying-out area A30 on the second story, paying-out devices 30 of two different types coexist in the paying-out area A30 on the second story.

As can be seen from FIGS. 1 and 2, in this example, the pairs of paying-out rotation shafts 32 of all of the paying-out devices 30 for the sheet-shaped materials 1ST on the first story and the second story are oriented in the Y-direction. Therefore, the sheet-shaped materials 1ST is paid out in the X-direction, that is, the sheet-shaped materials 1ST is paid out in a direction perpendicular to the flow direction D1 of the processing section 20. Thus, in this example, as illustrated in FIG. 3, a turn bar 50 for changing the direction of transport of the material 1ST that is paid out to the flow direction D1 is provided at a position between the paying-out rotation shaft 32 and the processing section 20.

Figure 10:
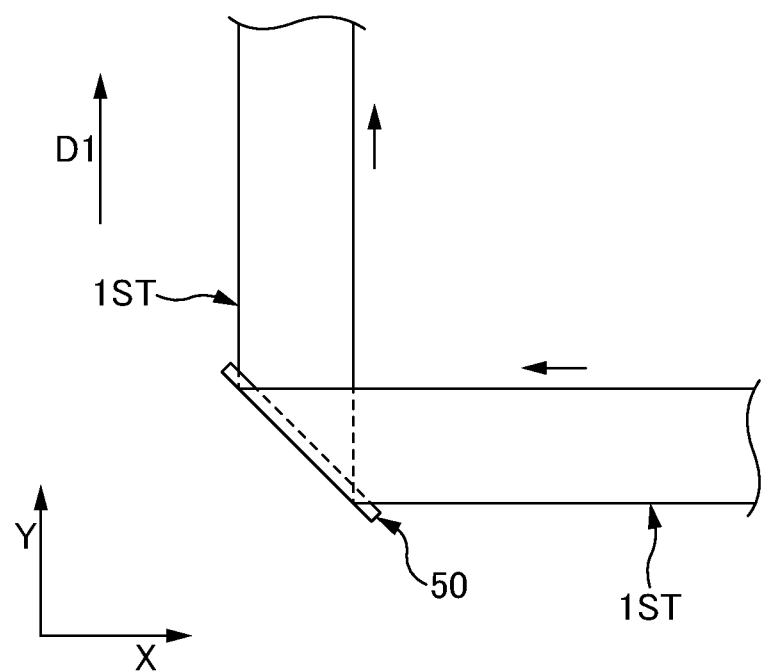
FIG. 10 is a schematic plan view of a turn bar 50 as viewed from above.

FIG. 10 is a schematic plan view of the turn bar 50 as viewed from above.

The turn bar 50 is an unrotatable bar-shaped member that is oriented in a direction inclined by 45° from both the X-direction and the Y-direction. Thus, by wrapping the material 1ST around the turn bar 50, the direction of transport of the material 1ST can be changed from the X-direction to the flow direction D1, which is the Y-direction.

In this example, a turn bar 50 for the material 1ST paid out from the paying-out device 30 on the second story is provided also on the first story. However, this is not a limitation. That is, the turn bar 50 may be provided on the second story. According to circumstances, the pair of paying-out rotation shafts 32 may be oriented in the X-direction. In this case, the material 1 is paid out in the flow direction D1, which is the Y-direction.

As illustrated in FIG. 8, basically, the nonwoven fabric 1NW paid out by the paying-out device 30 on the second story is transported by a plurality of transport rollers 41 disposed on the second story and reaches the communication opening 13uk in the floor 13u described above. Preferably, a transport roller 41f that the nonwoven fabric 1NW paid out from the paying-out device 30 first comes into contact with is located on the second story.

In this case, concerning the constituent fibers of the nonwoven fabric 1NW that have a low bonding strength and which may become lint, it is possible for most of such constituent fibers to come off and to be scattered, at the transport roller 41f on the second story that the nonwoven fabric 1NW first comes into contact with. Thus, it is possible to reduce the amount of lint that is scattered from the nonwoven fabric 1NW on the first story after the nonwoven fabric 1NW has been transported to the first story. Thus, it is possible to effectively prevent contamination of the first story with lint.

In view of causing a larger amount of lint to come off and to be scattered on the second story, preferably, a specific surface 1NWs2, which is one of two surfaces 1NWs1 and 1NWs2 of the nonwoven fabric 1NW in the thickness direction, comes into contact with the transport roller 41f. Hereafter, the specific surface 1NWs2 and the reason why the transport roller 41f preferably comes into contact with the specific surface 1NWs2 will be described.

Figure 11:
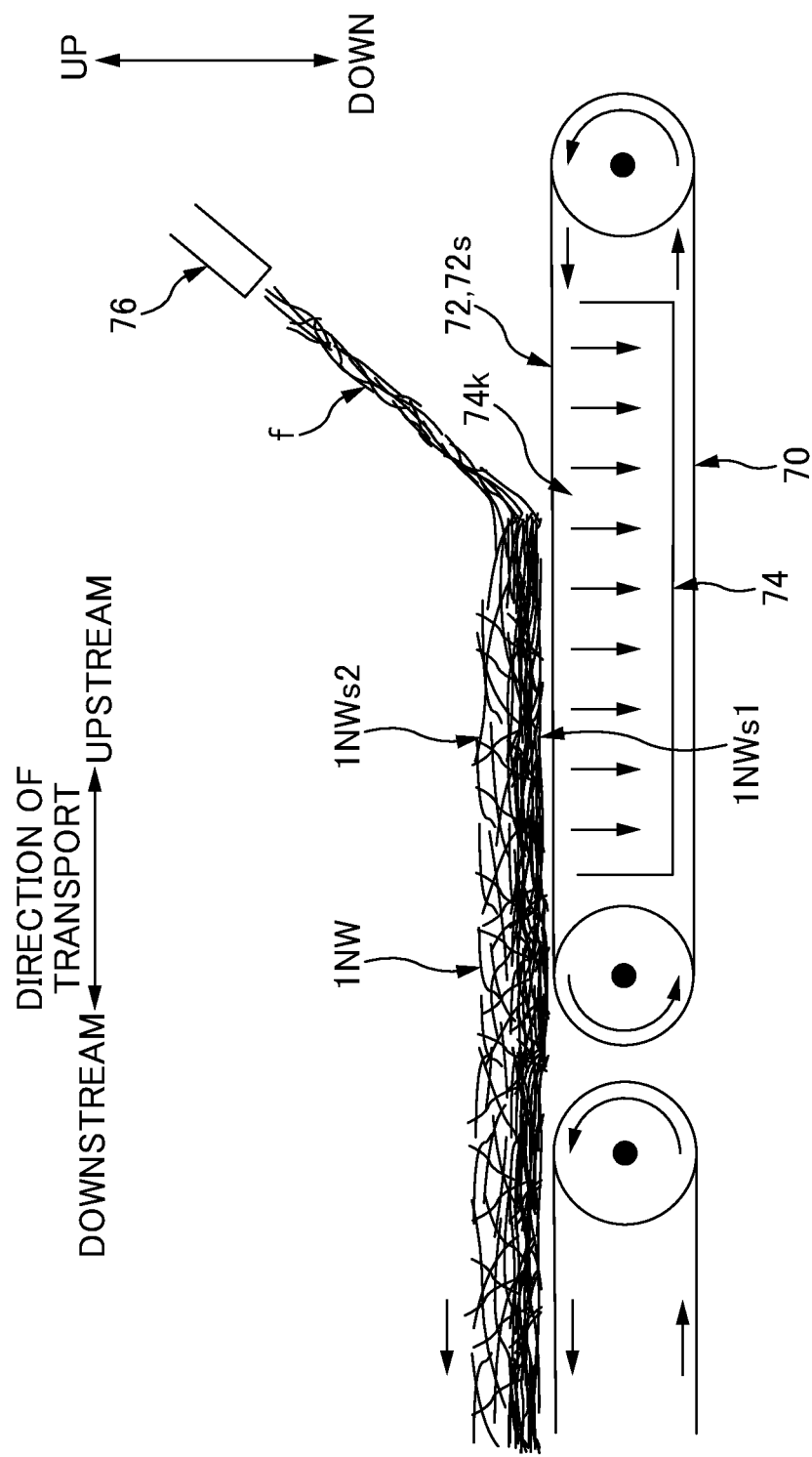
FIG. 11 is a schematic side view illustrating a process of producing a nonwoven fabric 1NW.

First, the nonwoven fabric 1NW is produced in a factory different from the factory 10. In the process of producing the nonwoven fabric 1NW performed in the other factory, the nonwoven fabric 1NW is produced by using a suction belt conveyer 70 as illustrated in a schematic side view of FIG. 11. Due to this process, the bonding strength of the constituent fibers of the produced nonwoven fabric 1NW has anisotropy in that the bonding strength at the non-abutting surface 1NWs2 that does not abut a net 72 (described below) of the suction belt conveyer 70 is lower than the bonding strength at the abutting surface 1NWs1 of the nonwoven fabric 1NW that abuts the net 72.

Therefore, in view of causing a larger amount of lint to come off and to be scattered from the nonwoven fabric 1NW on the second story of the factory 10 for manufacturing an absorbent article as described above, preferably, the contact surface of the nonwoven fabric 1NW that comes into contact with the transport roller 41f (FIG. 8) is the non-abutting surface 1NWs2 at which the bonding strength of the constituent fibers of the nonwoven fabric 1NW is low.

The reason why the bonding strength of the constituent fibers of the nonwoven fabric 1NW at the non-abutting surface 1NWs2 is lower than that at the abutting surface 1NWs1 is as follows.

First, the suction belt conveyer 70 includes the net 72 (corresponding to a support member) that circulates along a circulation path and that has an endless shape. The circulation path includes a flat path extending in a horizontal direction in an upper part thereof. Moreover, a suction box 74 is disposed inside the circulation path of the net 72, and an air inlet 74k sucks air at an upper part of the box 74. Thus, a suction force is generated at an upper surface 72s of the net 72.

Thus, when fibers f, which have been melt spun, are ejected toward the flat path from a nozzle 76 disposed above the upper surface 72s of the net 72, the fibers f are sucked onto and deposited on the upper surface 72s of the net 72. As a result, the nonwoven fabric 1NW is basically formed.

However, although a large suction force acts in a region near the upper surface 72s when the fibers f are deposited on the upper surface 72s of the net 72, the suction force decreases with increasing distance upward from the upper surface 72s. Therefore, the density of the fibers f is high on the upper surface 72s of the net 72, and thus the fibers f are bonded to each other with a high bonding strength. However, with increasing distance upward from the upper surface 72s, the density of the fibers f decreases, thereby decreasing the bonding strength of the fibers f. Thus, between the two surfaces 1NWs1 and 1NWs2 of the nonwoven fabric 1NW, the bonding strength of the fibers f at the non-abutting surface 1NWs2, which does not abut the upper surface 72s of the net 72, is lower than that at the abutting surface 1NWs1, which abuts the upper surface 72s of the net 72.

Other Embodiments

Although the embodiment of the present disclosure has been described hereinabove, the above embodiment of the present disclosure are simply to facilitate understanding of the present disclosure and are not in any way to be construed as limiting the present disclosure. The present disclosure may variously be changed or altered without departing from its gist and encompass equivalents thereof. For example, modification which will be described below is possible.

In the embodiment described above, as illustrated in FIG. 3, a building 12 having two full stories on or above the ground is described as an example of the building 12 of the factory 10 for manufacturing an absorbent article. However, this is not a limitation. That is, the number of stories may be three or more. In this case, the upper story and the lower story are not limited to the second story and the first story and may be the third story and the second story, or may be the fourth story and the third story. Further, the stories of the two-story building are not limited to two stories on or above the ground. That is, a building with two full stories may be composed of a belowground story and a ground story.

In the embodiment described above, as illustrated in FIGS. 1 and 2, the first story and the second story are respectively surrounded by four walls 14$d$ and four walls 14$u$. However, the concepts of the walls 14$d$ and 14$u$ include walls formed of gas, such as so-called air curtains, in addition to solid walls such as reinforced concrete walls, wooden walls, and metal panels. Thus, for example, one or more of the four walls 14$d$ and the four walls 14$u$ may be air curtains.

In the embodiment described above, as illustrated in FIGS. 1 and 2, a rectangular shape is described as an example of the planar shape of each of the floors 13$d$ and 13$u$ on the first story and the second story. However, this is not a limitation. For example, the planar shape may be a polygon, such as a hexagon, or a circle. The planar shape may have concave corners or convex corners. Also in such cases, each of the walls is provided to correspond to one of the sides of the planar shape.

In the embodiment described above, as illustrated in FIG. 2, because each of the paying-out devices 30 in the paying-out area A30 on the second story pays out the nonwoven fabric 1NW in the X-direction, the planar shape of each of the communication openings 13$uk$ is a substantially rectangular shape whose longitudinal direction is the Y-direction. However, this is not a limitation. For example, if any of the paying-out devices 30 pays out the nonwoven fabric 1NW in the X-direction, the planar shape of the communication opening 13$uk$ corresponding to this device 30 may be a substantially rectangular shape whose longitudinal direction is the X-direction. According to circumstances, the planar shape of the communication opening 13$uk$ may be a polygon, a circle, or an elongated circle, or may be a composite shape in which straight lines and curved lines are combined.

REFERENCE SIGNS LIST 1 material,
1C material coil,
1NW nonwoven fabric
1CNW material coil,
1NWs1 abutting surface
1NWs2 non-abutting surface,
1NN non-nonwoven-fabric material
1CNN material coil,
1SG string-shaped material
1CSG material coil,
1ST sheet-shaped material
1CST material coil,
1STes leading end
3 double-sided tape
10 factory,
12 building,
13$d$ floor,
13$u$ floor
13$uk$ communication opening (opening)
14$d$ wall,
14$u$ wall,
15 roof,
16$d$ wall,
16$dk$ opening,
16$u$ wall
20 processing section,
22 processing device,
23B base portion,
23K plate portion
30 paying-out device,
30SGA support shaft
32 paying-out rotation shaft
33B base portion,
33K plate portion
34$a$ pressing device,
34$b$ cutting device
35$a$ pressing device,
35$b$ cutting device
40 material accumulation device
41 transport roller,
41$f$ transport roller
41$a$ fixed-position roller,
41$b$ mobile roller
45 turret,
50 turn bar,
70 suction belt conveyer,
72 net
72$s$ upper surface,
74 suction box,
74$k$ air inlet
76 nozzle,
A1C storage area,
A30 paying-out area
PBd boundary position,
PBu boundary position,
f fiber

The invention claimed is:

1. A factory for manufacturing an absorbent article by using a plurality of types of materials, comprising:
a building including:
an upper story; and
a lower story located below the upper story, wherein
the upper story comprises: a floor; a wall provided along an entire periphery of the floor; an illumination device provided on a ceiling; and an air conditioner having an air outlet for discharging air,
the lower story comprises: a floor; a wall provided along an entire periphery of the floor; an illumination device provided on a ceiling; and an air conditioner having an air outlet for discharging air; and
an opening through which the upper story and the lower story communicate is formed in the floor of the upper story, wherein
the upper story further comprises a paying-out device to which a material coil on which a nonwoven fabric is wound is attached and that pays out the nonwoven fabric, the nonwoven fabric serves as at least one type among the plurality of types of materials, the lower story further comprises a processing section that processes the plurality of types of materials including the nonwoven fabric that is transported from the upper story through the opening, and an air pressure at a boundary position between a space on the lower story and the opening is higher than an air pressure at a boundary position between a space on the upper story and the opening.

2. The factory for manufacturing an absorbent article according to claim 1, wherein all types of nonwoven fabrics that the plurality of types of materials include besides the nonwoven fabric are respectively brought into the building in forms of material coils in which the nonwoven fabrics are wound, paying-out devices respectively corresponding to all of the types of nonwoven fabrics are provided on the upper story, and the paying-out devices pays out the corresponding nonwoven fabrics from the material coils.

3. The factory for manufacturing an absorbent article according to claim 1, wherein the lower story further includes a paying-out device to which a material coil on which a non-nonwoven-fabric material is wound is attached and that pays out the non-nonwoven-fabric material, and the non-nonwoven-fabric material is a material that is not a nonwoven fabric and serves as at least one type among the plurality of types of materials.

4. The factory for manufacturing an absorbent article according to claim 1, wherein the plurality of types of materials are respectively brought into the building in forms of material coils in which the materials are wound, the material coils are attached to paying-out devices that respectively correspond to the plurality of types of materials, the materials are paid out from the material coils, and among the material coils of the plurality of types of materials, a material coil to be paid out by the paying-out device on the upper story is stored in a storage area on the upper story, and among the material coils of the plurality of types of materials, a material coil to be paid out by the paying-out device on the lower story is stored in a storage area on the lower story.

5. The factory for manufacturing an absorbent article according to claim 4, wherein a wall is provided between a paying-out area in which the paying-out device is provided on the upper story and the storage area on the upper story, and a wall is provided between a paying-out area in which the paying-out device is provided on the lower story and the storage area on the lower story.

6. The factory for manufacturing an absorbent article according to claim 1, wherein a transport roller that the nonwoven fabric paid out from the material coil by the paying-out device on the upper story first comes into contact with is located on the upper story, and a contact surface of the nonwoven fabric that comes into contact with the transport roller is a non-abutting surface that does not abut a support surface of a support member when constituent fibers of the nonwoven fabric are sucked onto and deposited on the support surface to produce the nonwoven fabric.

7. The factory for manufacturing an absorbent article according to claim 1, wherein an amount ($g/m^3$) of fibers included in a unit volume at a boundary position between a space on the lower story and the opening is smaller than an amount ($g/m^3$) of fibers included in a unit volume at a boundary position between a space on the upper story and the opening.

8. The factory for manufacturing an absorbent article according to claim 1, wherein when the building is viewed in cutaway from above, the opening is disposed in such a way that at least a part of the opening overlaps the processing section.

9. The factory for manufacturing an absorbent article according to claim 1, wherein when the building is viewed in cutaway from above, the paying-out device that pays out the nonwoven fabric is disposed in such a way that at least a part of the paying-out device overlaps the processing section.

10. The factory for manufacturing an absorbent article according to claim 1, wherein when the nonwoven fabric is defined as a first nonwoven fabric, the material coil on which the nonwoven fabric is wound is defined as a first material coil, and the paying-out device for the nonwoven fabric is defined as a first paying-out device:

the plurality of types of materials include a second nonwoven fabric that is different from the first nonwoven fabric, the upper story further includes a second paying-out device to which a second material coil on which the second nonwoven fabric is wound is attached and that pays out the second nonwoven fabric, the first paying-out device includes:

a paying-out rotation shaft to which the first material coil that is a preceding first material coil is attached; and a paying-out rotation shaft to which the first material coil that is a succeeding first material coil is attached, the first paying-out device has a material splicing function of splicing the first nonwoven fabric of the succeeding first material coil with the first nonwoven fabric of the preceding first material coil in a state in which rotation of the paying-out rotation shaft to which the preceding first material coil is attached and rotation of the paying-out rotation shaft to which the succeeding first material coil is attached are both stopped, the first nonwoven fabric is accumulated in a form of a plurality of loops using a plurality of rollers that are disposed on the upper story between the first paying-out device and the processing section, while rotation of the paying-out rotation shafts is stopped, the first nonwoven fabric is supplied to the processing section by reducing sizes of the plurality of loops of the first nonwoven fabric, the second paying-out device includes:

a paying-out rotation shaft to which the second material coil that is a preceding second material coil is attached; and a paying-out rotation shaft to which the second material coil that is a succeeding second material coil is attached, and the second paying-out device has a material splicing function of splicing the second nonwoven fabric of the succeeding second material coil with the second nonwoven fabric of the preceding second material coil in a state in which the paying-out rotation shaft to which the preceding second material coil is attached and the paying-out rotation shaft to which the succeeding second material coil is attached both rotate.

\* \* \* \* \*